United States Patent
Ravenscroft et al.

[11] Patent Number: 6,110,192
[45] Date of Patent: Aug. 29, 2000

[54] CATHETER BALLOON HAVING RAISED RADIAL SEGMENTS

[75] Inventors: Adrian Ravenscroft, Lower Mills; Donna Lin, Weston, both of Mass.

[73] Assignee: Boston Scientific Corporation, Natick, Mass.

[21] Appl. No.: 09/226,986

[22] Filed: Jan. 8, 1999

Related U.S. Application Data

[63] Continuation of application No. 08/710,815, Sep. 23, 1996, Pat. No. 5,954,740.

[51] Int. Cl.$^7$ ................................................. A61M 29/00
[52] U.S. Cl. ............................................. 606/194; 604/96
[58] Field of Search .................... 606/1, 108, 192, 606/194, 198; 604/96–101

[56] References Cited

U.S. PATENT DOCUMENTS

| | | |
|---|---|---|
| 2,330,399 | 9/1943 | Winder . |
| 2,486,056 | 10/1949 | Oclassen . |
| 3,409,016 | 11/1968 | Foley . |
| 3,557,794 | 1/1971 | Van Patten . |
| 3,822,593 | 7/1974 | Oudewaal . |
| 4,018,231 | 4/1977 | Wallace . |
| 4,141,364 | 2/1979 | Schultze . |
| 4,178,939 | 12/1979 | Stephens . |
| 4,248,246 | 2/1981 | Ikeda . |
| 4,275,591 | 6/1981 | Wand . |
| 4,276,874 | 7/1981 | Wolvek et al. . |
| 4,292,974 | 10/1981 | Fogarty et al. . |
| 4,346,698 | 8/1982 | Hanson et al. . |
| 4,416,267 | 11/1983 | Garren et al. . |
| 4,444,186 | 4/1984 | Wolvek et al. . |
| 4,449,532 | 5/1984 | Storz . |
| 4,572,186 | 2/1986 | Gould et al. . |
| 4,573,470 | 3/1986 | Samson et al. . |
| 4,576,142 | 3/1986 | Schiff . |
| 4,592,744 | 6/1986 | Jagger et al. . |
| 4,601,713 | 7/1986 | Fuqua . |
| 4,636,201 | 1/1987 | Ambrose et al. . |
| 4,681,092 | 7/1987 | Cho et al. . |
| 4,710,181 | 12/1987 | Fuqua . |
| 4,738,666 | 4/1988 | Fuqua . |
| 4,743,258 | 5/1988 | Ikada et al. . |
| 4,762,125 | 8/1988 | Leiman et al. . |
| 4,762,130 | 8/1988 | Fogarty et al. . |
| 4,771,776 | 9/1988 | Powell et al. . |
| 4,796,629 | 1/1989 | Grayzel . |
| 4,820,349 | 4/1989 | Saab . |
| 4,846,174 | 7/1989 | Willard et al. . |
| 4,846,344 | 7/1989 | Bala . |
| 4,846,801 | 7/1989 | Okuda et al. . |
| 4,881,547 | 11/1989 | Danforth . |
| 4,896,669 | 1/1990 | Bhate et al. . |
| 4,906,244 | 3/1990 | Pinchuk et al. . |
| 4,921,483 | 5/1990 | Wijay et al. . |
| 4,930,341 | 6/1990 | Euteneuer . |

(List continued on next page.)

FOREIGN PATENT DOCUMENTS

| | | |
|---|---|---|
| 0 414 350 A1 | 2/1991 | European Pat. Off. . |
| 0 414 350 B1 | 2/1991 | European Pat. Off. . |
| 1 170 586 | 5/1964 | Germany . |
| WO 92/19306 | 11/1992 | WIPO . |
| WO 95/00198 | 1/1995 | WIPO . |
| WO 95/05860 | 3/1995 | WIPO . |

*Primary Examiner*—Michael Buiz
*Assistant Examiner*—William Lewis
*Attorney, Agent, or Firm*—Crompton, Seager & Tufte, LLC

[57] ABSTRACT

A dilation balloon for a catheter with improved folding characteristics for insertion into a body conduit. The balloon surface is generally textured, having a reduced texture longitudinal strip causing preferential controlled folding along the strip. The preferential folding creates curved wings which fold together upon further deflation. The curved, folded wings result in a decreased profile having wing edges oriented so as to decrease contact with conduit walls. A preferred embodiment has raised radial ridges extending around a portion of the circumference of the balloon and a smooth longitudinal surface radially therebetween.

5 Claims, 4 Drawing Sheets

U.S. PATENT DOCUMENTS

| | | |
|---|---|---|
| 4,935,190 | 6/1990 | Tennerstedt . |
| 4,938,676 | 7/1990 | Jackowski et al. . |
| 4,941,877 | 7/1990 | Montano, Jr. . |
| 4,994,072 | 2/1991 | Bhate et al. . |
| 5,015,230 | 5/1991 | Martin et al. . |
| 5,015,231 | 5/1991 | Keith et al. . |
| 5,017,325 | 5/1991 | Jackowski et al. . |
| 5,037,392 | 8/1991 | Hillstead . |
| 5,041,125 | 8/1991 | Montano, Jr. . |
| 5,087,246 | 2/1992 | Smith . |
| 5,147,302 | 9/1992 | Euteneuer et al. . |
| 5,192,296 | 3/1993 | Bhate et al. . |
| 5,195,970 | 3/1993 | Gahara . |
| 5,196,024 | 3/1993 | Barath . |
| 5,209,799 | 5/1993 | Vigil . |
| 5,226,887 | 7/1993 | Farr et al. . |
| 5,250,070 | 10/1993 | Parodi . |
| 5,254,091 | 10/1993 | Aliahmad et al. . |
| 5,295,995 | 3/1994 | Kleiman . |
| 5,306,246 | 4/1994 | Sahatjian et al. . |
| 5,308,356 | 5/1994 | Blackshear, Jr. et al. . |
| 5,318,587 | 6/1994 | Davey . |
| 5,320,634 | 6/1994 | Vigil et al. . |
| 5,336,178 | 8/1994 | Kaplan et al. . |
| 5,342,301 | 8/1994 | Saab . |
| 5,342,307 | 8/1994 | Euteneuer et al. . |
| 5,350,361 | 9/1994 | Tsukashima et al. . |
| 5,366,472 | 11/1994 | Hillstead . |
| 5,370,614 | 12/1994 | Amundson et al. . |
| 5,411,477 | 5/1995 | Saab . |
| 5,423,745 | 6/1995 | Todd et al. . |
| 5,456,666 | 10/1995 | Campbell et al. . |
| 5,458,572 | 10/1995 | Campbell et al. . |
| 5,470,313 | 11/1995 | Crocker et al. . |
| 5,478,319 | 12/1995 | Campbell et al. . |
| 5,490,839 | 2/1996 | Wang et al. . |
| 5,658,311 | 8/1997 | Baden . |
| 5,718,684 | 2/1998 | Gupta . |

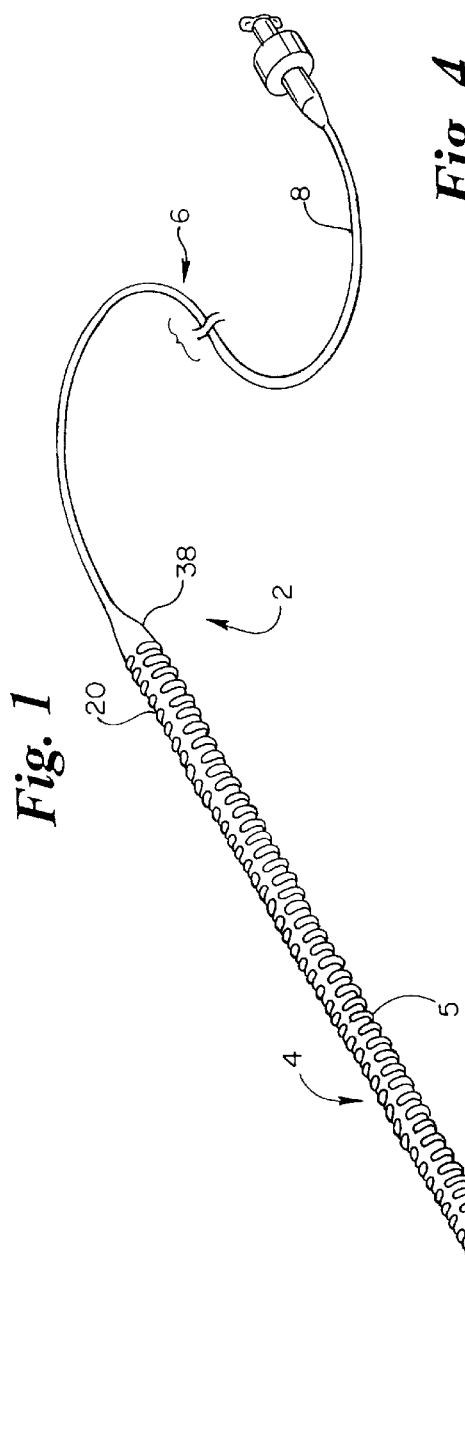
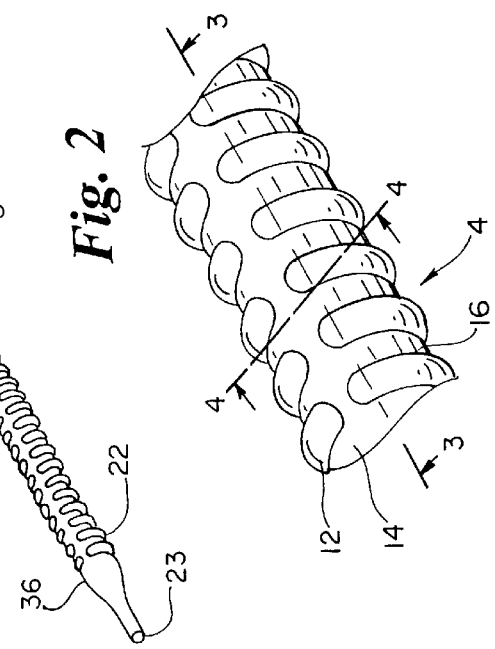
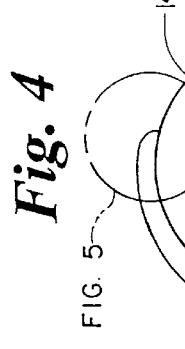
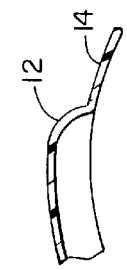

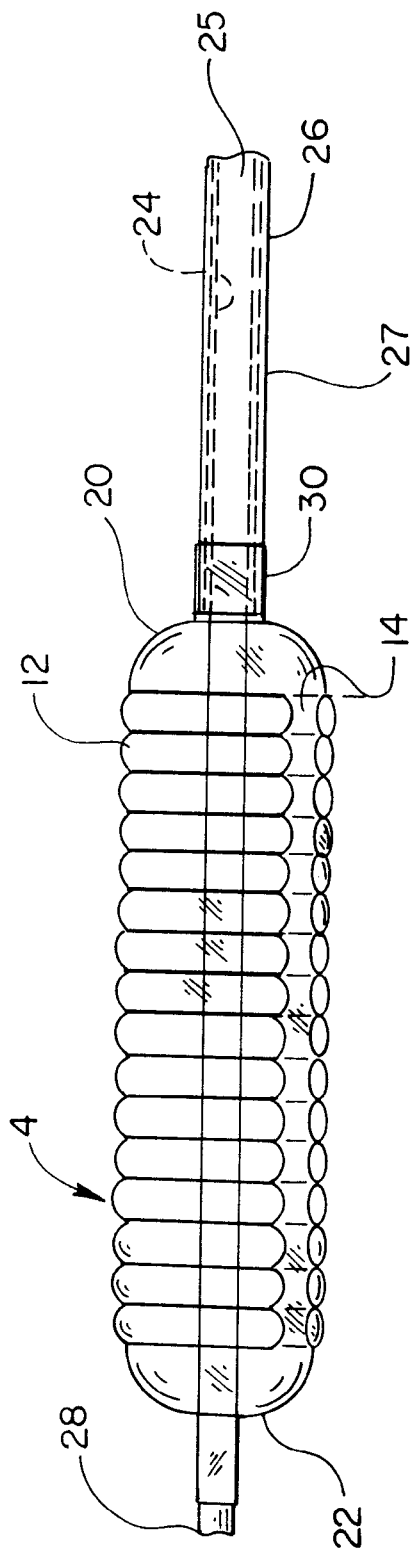

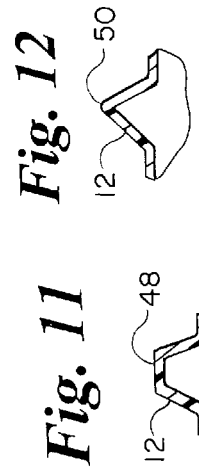
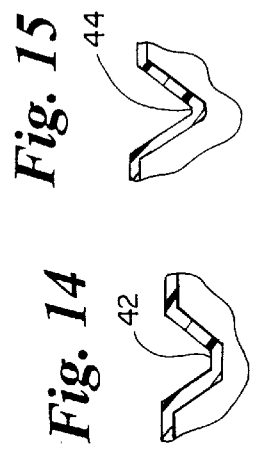
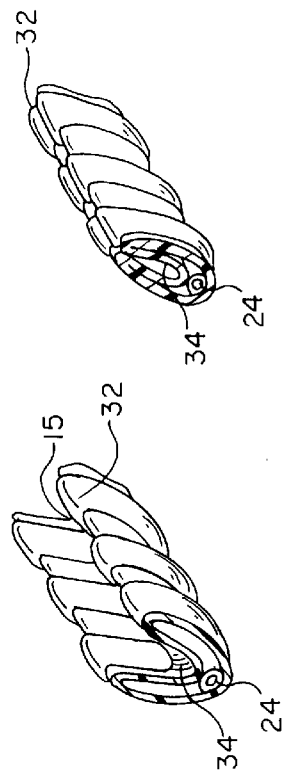

CATHETER BALLOON HAVING RAISED RADIAL SEGMENTS

This application is a continuation of U.S. patent application Ser. No. 08/710,815, filed Sep. 23, 1996, now U.S. Pat. No. 5,954,740.

FIELD OF THE INVENTION

The present invention relates to catheters for performing intravascular and non-intravascular medical procedures, wherein an expandable balloon is mounted proximate the distal end of the catheter. More specifically, the invention relates to a balloon design incorporating a textured surface and at least one reduced texture longitudinal strip to achieve improved folding characteristics.

BACKGROUND OF THE INVENTION

Percutaneous transluminal angioplasty (PTA) is a well established procedure for the treatment of blockages in arteries. Blockages may occur from cholesterol buildup on the artery wall which may be in any stage from initial deposit through aged lesions. Arteries can also become blocked due to formation of thrombus.

The most widely used form of PTA makes use of a dilation balloon catheter, which has an expandable or inflatable balloon member proximate its distal end. The catheter is inserted into the patient's vascular system and guided until the balloon at the distal end of the catheter is positioned across a stenosis or blockage. A fluid is then fed under pressure through an inflation lumen of the catheter to the balloon, which causes the balloon to expand outward, thereby opening the stenosis.

Another use for balloon catheters is the placement of stents, grafts or stent/graft composites. To put a stent into position, the stent is placed around the balloon, and the balloon advanced into position within a vessel. The balloon is then inflated, expanding the stent outward against the vessel wall and into the desired shape and size. The balloon is deflated, leaving the stent in place. Balloons having smooth surfaces sometimes have difficulty in achieving separation of the balloon surface from the stent during balloon deflation. The smooth balloon surface has the potential to stick to the stent or graft. Sticking is more of problem with some materials, such as glassy PTFE, than others.

One important characteristic of a dilation balloon used for angioplasty or stent placement is its profile, which is determined by the outer diameter of the distal end portion of the catheter and the balloon cross section. The outer diameter of the dilation balloon, both before inflation, during insertion and after treatment upon deflation, affects the ease and ability of the dilation catheter to pass through a guide catheter, through small caliber or small lumen arteries, and across a tight lesion. It is desirable to have a catheter having a low profile when the balloon is initially inserted uninflated and after treatment upon deflation for ease in both insertion and withdrawal.

In order to reduce the outer diameter of the balloon in its pre-inflation condition, it is common to fold the balloon flat, resulting in two wings being formed. These two wings are sometimes brought together in some fashion so as to reduce the overall diameter of the deflated balloon. This is commonly done by installing a sleeve or balloon protector around the deflated balloon to bring the two wings together. After inflation during treatment, it is often difficult to return balloon wings to their pre-inflation configuration. This becomes a problem when the balloon does not return to a diameter small enough to fit within the guide catheter, or pass across a tight lesion in multi-site angioplasty.

After dilation, the balloon is deflated by pulling vacuum on the balloon, collapsing the balloon, often referred to as "pancaking", forming flat wings having edges at their outermost extent. A non-elastic balloon having inflated diameter D, will have a post-inflation pancaked flat cross section of about $Pi*D$, a significant increase. The presence of wings and edges can interfere with ease of retraction, both through a guide catheter and through a body vessel or through a deployed implant such as a stent or graft. A smaller profile upon deflation is more desirable than a larger profile because of the increased ease of retraction and decreased contact with vessel walls. Various approaches have been taken to reduce the profile of balloons prior to retraction as summarized below.

Campbell et al. (U.S. Pat. No. 5,478,319) disclose a balloon having four longitudinal ribs, providing for four smaller wings upon deflation rather than two larger wings.

Hilstead (U.S. Pat. No. 5,366,472) discloses a dilation catheter having an elastic sleeve to expand with the balloon and contain the balloon wings after deflation.

Tsukashima et al. (U.S. Pat. No. 5,350,361) disclose a balloon having three smaller wings upon deflation rather than two larger wings.

Many of the folding improvements result in deflated balloons still having flat wings, albeit smaller ones, and still having outwardly projecting wing edges. There remains a need for a catheter balloon with improved folding characteristics. There also remains a need for a catheter balloon having improved, non-stick characteristics for stent and graft placement.

SUMMARY OF THE INVENTION

The present invention is a medical dilation balloon for insertion into a body conduit. More specifically, the invention includes a balloon having improved folding characteristics, providing a smaller and easier to withdraw profile upon deflation. The present invention uses an angioplasty balloon catheter by way of example, but other medical dilation catheters are within the scope of the invention.

The balloon of the present invention includes a textured surface and at least one reduced-texture longitudinal strip. The preferred embodiment includes raised radial ridges and a single longitudinal notch or strip which does not have radial ridges. In another embodiment, the longitudinal strip has radial ridges of reduced height or density. In combination, the textured-surface and reduced-texture longitudinal strip operate to cause controlled preferential folding along the reduced-texture strip, leading to an initial controlled folding along the strip caused by an initial collapse of the longitudinal notch. The controlled folding is followed by formation of wings. The wings curl and draw closer together upon further deflation. In the preferred embodiment having a single longitudinal strip, the wings curl and draw together at their tips. The curling of the wings dispose the wing edges inward and less disposed toward the conduit or blood vessel walls. This presents a more rounded surface to the conduit wall than the edges of a flat pancaked balloon.

The present invention can also include a coaxial catheter shaft having an inner shaft attached to the balloon distal end and an outer shaft attached to the balloon proximal end. This coaxial shaft allows for change in the longitudinal dimension of the balloon during inflation and deflation with reduced bending of the balloon.

The present invention includes a balloon for attachment to a shaft, and an assembly including both balloon and shaft. Use of the present balloon for graft and stent placement is also contemplated. The balloon of the present invention may be used particularly advantageously with grafts formed of graft material such as polytetrafluoroethylene, collagen or composites.

BRIEF DESCRIPTION OF THE DRAWINGS

The present invention is illustrated by way of example and not limitation in the figures of the accompanying drawings in which like references indicate similar parts and in which:

FIG. 1 is a perspective view of a balloon catheter assembly including a balloon incorporating a preferential folding design;

FIG. 2 is an enlarged perspective view of the balloon surface depicted in FIG. 1;

FIG. 3 is an enlarged fragmentary cross-sectional view taken along lines 3—3 of FIG. 2, illustrating a balloon surface having raised radial ridges;

FIG. 4 is a cross-sectional view of a relaxed balloon taken along lines 4—4 of FIG. 2, illustrating a raised radial ridge and reduced texture longitudinal strip;

FIG. 5 is an enlarged fragmentary cross-sectional view of the circled area of FIG. 4;

FIG. 6 is a side elevational view illustrating a balloon of the present invention as mounted on catheter shafts;

FIG. 10 is a cross-sectional view of a rounded ridge apex taken along a plane perpendicular to the balloon longitudinal axis;

FIG. 11 is a cross-sectional view of a flat ridge apex taken along a plane perpendicular to the balloon longitudinal axis;

FIG. 12 is a cross-sectional view of a pointed ridge apex taken along a plane perpendicular to the balloon longitudinal axis;

FIG. 13 is a cross-sectional view of a rounded trough apex taken along a plane perpendicular to the balloon longitudinal axis;

FIG. 14 is a cross-sectional view of a flat trough apex taken along a plane perpendicular to the balloon longitudinal axis;

FIG. 15 is a cross-sectional view of a pointed trough apex taken along a plane perpendicular to the balloon longitudinal axis;

FIG. 16 is a fragmentary perspective view of a balloon in an early stage of deflation;

FIG. 17 is a fragmentary perspective view of a balloon in a further stage of deflation;

FIG. 18 is a fragmentary perspective view of a balloon in a still further stage of deflation;

FIG. 19 is a fragmentary perspective view of a balloon in an even further stage of deflation;

DETAILED DESCRIPTION OF THE PREFERRED EMBODIMENTS

Figure 7:
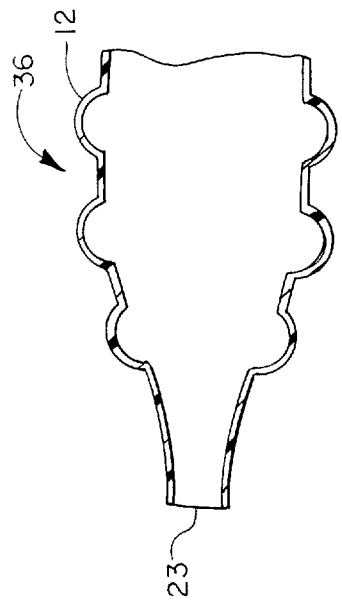
FIG. 7 is an enlarged cross-sectional view of an alternative balloon distal transition section.

FIG. 1 illustrates generally a dilation balloon catheter 2 of the present invention having a catheter shaft 6 attached distally to a balloon 4. Shaft 6 includes a shaft proximal end 8, and balloon 4 includes a balloon proximal end 20, distal end 22, and distal tip 23. Balloon 4 includes a distal transition or waist section 36 proximal to distal tip 23 and proximal transition or waist section 38 distal to the junction of catheter shaft 6 to balloon 4. As defined herein, the balloon 4 includes a balloon envelope 5 which defines the balloon between the distal waist 36 and proximal waist 38. In a preferred embodiment, as illustrated in FIG. 6, the shaft includes an inner shaft 24 coaxially disposed within an outer shaft 26. The inner shaft 24 extends the length of the catheter to provide a guide wire lumen 25 for guiding the catheter over a guide wire (not shown). The annular space formed between inner shaft 24 and outer shaft 26 forms an inflation lumen 27 in fluid communication with the balloon 4.

Balloon 4 can exist in different stages of inflation including pressurized (inflated), non-pressurized (relaxed), and under vacuum (deflated). In the pressurized state, inflation fluid under pressure causes balloon 4 to expand. In the non-pressurized state, balloon 4 is not flat, having retained some structure. A non-pressurized balloon outside the body may have much of its full profile. A non-pressurized balloon inserted across a tight stenosis may have a significantly smaller profile, requiring pressurization to press outward against the stenosis and attain a full profile. When under vacuum, the inflation fluid has been withdrawn, pulling vacuum, causing balloon 4 to deflate and decrease in size.

FIG. 2 illustrates a section of balloon envelope surface 16 in a relaxed state, this embodiment having a textured surface comprising raised radial ridges 12. The raised radial ridges 12 extend around a portion of the circumference of the balloon surface 16. A reduced texture strip, comprising a longitudinal strip 14 extends longitudinally along at least a portion of the balloon surface 16. In a preferred embodiment, the longitudinal strip 14 is a relatively smooth surface simply lacking the raised radial ridges 12 which terminate at both sides of the longitudinal strip 14. In another embodiment, longitudinal strip 14 includes raised radial ridges having reduced ridge height or density.

FIG. 3 shows an enlarged view of balloon envelope surface 16 and raised radial ridges 12. The embodiment of FIG. 3 includes radial ridges having relatively uniform ridge width and height. This embodiment has peaks 15 and troughs 17, with troughs 17 being at generally the same height or radial distance as balloon surface 16 and longitudinal strip 14. Described alternatively, peaks 15 may be considered generally the same height as the balloon surface, with troughs 17 described as being below the balloon surface. A preferred embodiment has 1 to 50 ridges per inch in the longitudinal direction. A most preferred embodiment has 10 to 20 ridges per inch.

FIG. 4 shows another view of one raised radial ridge 12 and longitudinal strip 14. FIG. 5 shows an enlarged view of one raised radial ridge 12 and longitudinal strip 14. As depicted in these views, the raised radial ridges 12 are formed integral with the balloon as can be done with standard blow molding.

FIG. 6 illustrates balloon 4 in a related state, not under vacuum. Catheter shaft 6 is shown having an inner shaft 24 coaxially within an outer shaft 26. Inner shaft 24 is attached to balloon distal end 22 at inner shaft distal end 28 and outer shaft 26 is attached to balloon proximal end 20. The inner shaft 24 can be axially slidable within outer shaft 26 or may be fixed relative to the outer shaft 26 at the proximal end of the catheter. In one embodiment of the invention, inner shaft distal end 28 is bonded to balloon distal end 22 and outer shaft 26 is bonded to balloon proximal end 20. The attachment of the balloon to the shafts serves to contain inflation fluid. The balloon may be bonded to the shafts by adhesive. The embodiment of FIG. 6 depicts longitudinal strip 14 running in a straight line parallel to the longitudinal axis of the balloon. Alternatively, the longitudinal strip can run in a spiral around balloon surface 16.

FIG. 7 illustrates an embodiment having raised radial ridges 12 in distal transition or waist section 36. Other embodiments (not shown) can have raised radial ridges in the proximal transition or waist section 38. Other embodiments, as illustrated in FIG. 6, have no raised radial ridges in either transition section.

Figure 8:
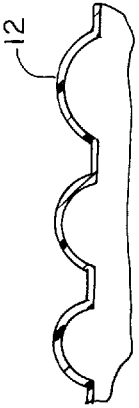
FIG. 8 is an enlarged cross-sectional view of ridges having rounded apexes of varying width and height.
Figure 9:
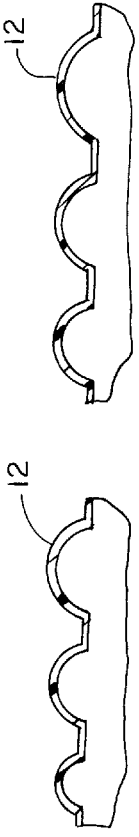
FIG. 9 is an enlarged cross-sectional view of ridges having rounded apexes of varying width.

Balloons having varying radial ridge height and width are within the scope of the invention. FIG. 8 illustrates an embodiment including raised radial ridges 12 having rounded apexes varying in both width and height. FIG. 9 illustrates an embodiment including raised radial ridges 12 having rounded apexes of varying width.

Various ridge apex shapes are also within the scope of the invention. FIG. 10 illustrates an embodiment having raised radial ridges 12 with a rounded ridge apex 46. FIG. 11 illustrates another embodiment having a flat ridge apex 13. FIG. 12 illustrates yet another embodiment having a pointed ridge apex 12.

Various radial trough apex shapes are also within the scope of the invention. FIG. 13 illustrates an embodiment having a rounded trough apex 40. FIG. 14 illustrates another embodiment having a flat trough apex 42. FIG. 15 illustrates yet another embodiment having a pointed trough apex 44.

When relaxed and not otherwise constricted, balloon 4 appears as illustrated in FIGS. 2 and 6, having a surface texture such as the raised radial ridges 12 shown. This surface functions in combination with a region with reduced surface texture, as illustrated by longitudinal strip 14. Many surface textures provide a similar function, including (not shown) cross cuts, hatching, scalloping, and ball peening marks.

When fully pressurized, balloon 4 envelopes surfaces 16 and radial ridges 12 flattened out, reducing or eliminating the height difference of balloon envelope surface 16 and radial ridges 12. This flattened, pressurized balloon surface, when used for stent placement, serves to uniformly expand the stent into the vessel walls. Once the angioplasty or placement is complete, balloon deflation may begin.

The region with reduced surface texture serves as a region of structural weakness during deflation relative to the textured region. This region initiates a controlled preferential collapse or folding of the inflated balloon when deflation occurs. In preferred embodiments, the region of reduced surface texture is a longitudinal strip 14 or a longitudinal notch 15. A balloon may have one or more notches. The length of a notch may be from 0.5 mm to the entire length of the balloon. A preferred embodiment has a single longitudinal strip or notch of reduced texture. The apex of the notch may be pointed, angular, smooth or rounded. A preferred embodiment as depicted in FIGS. 2 and 6, includes a smooth longitudinal strip which is formed during blow molding by simply terminating the raised radial ridges prior to encircling the entire balloon circumference. Alternatively, the angles of the sides of the notch may form a generally equilateral or isosceles triangular shape. Notch sides may be angular, curved, or radiused. Notches may be continuous or intermittent across the balloon length. Notches can be generally parallel to the balloon body longitudinal axis as illustrated in FIG. 16. Notches can also spiral around the balloon body, take a curved path, or fall at an angle across the balloon length.

When inflated, a balloon embodying this invention will lengthen. This lengthening may be more pronounced on a balloon cylindrical surface opposite a longitudinal ridge. The ridges can act as bellows adding length to the balloon, with bending where ridges are less pronounced, as on a reduced texture strip. This lengthening, when coupled with an axially fixed shaft, will tend to bend the balloon in a curved or banana shape, as the balloon ends are fixed and the balloon is lengthening. In a balloon having a perfectly symmetrical surface, the direction of this bending will be unpredictable. In the present invention, this bending will be concave on a balloon surface having a longitudinal strip. The longitudinal strip will assume a concave orientation in the resulting banana shape. The banana-like shape will range from very slight to pronounced in different embodiments of the invention having an axially fixed shaft.

The balloon bending may be used advantageously where such bending is a benefit, as in conforming to an anatomical curve in a selected artery. Balloon bending may also be reduced by compensating for the bend by molding the balloon such that it has a bend in a direction to counter the pressurized bending.

In embodiments where balloon bending is not desired, such bending can be mitigated or eliminated using a coaxial shaft design. The increased balloon length can be accommodated by the coaxial shaft design as depicted in FIG. 6, having outer shaft 26 axially moveable relative to inner shaft 24, allowing for balloon elongation without significant balloon bending.

Upon initial depressurization, the region of reduced surface texture or longitudinal strip 14 collapse to form notch 15 which acts as a living hinge and collapses toward the center shaft, as illustrated in FIG. 16. The notch controls where the balloon will initially collapse, providing a deterministic, controlled folding of the deflating balloon. The embodiment shown in FIG. 16 has a generally V-shaped notch.

Upon depressurizing, a balloon envelope without surface texture would tend to collapse in an uncontrolled manner, leading to "pancaking" and a totally collapsed balloon having wings. The textured balloon surface and notch 15 bring about a controlled collapse, as illustrated in FIG. 17. In the present invention, the strip of reduced texture 14 which formed longitudinal notch 15 serves as a global region of weakness, causing preferential and controlled folding along the notch 15. This preferential folding along a non-textured longitudinal strip occurs because the longitudinal strip lacks the same three dimensional structural support provided by the texture structure. As deflation further continues, this controlled folding continues, causing more of the balloon surface adjacent to the longitudinal strip to become part of a radially inward oriented notch or channel. As deflation continues further, this notch becomes deeper, forming two slightly curved wings having longitudinal edges 32 as depicted in FIG. 17.

The partially deflated balloon notch initiates a corresponding folding of the balloon envelope surface 16 on either side of the notch, resulting in two longitudinal edges 32 illustrated in FIGS. 17 and 18. In many prior art balloons, the longitudinal edges 32 would be on either side of the "pancake", forming the outermost edges of the balloon wings. In the present invention, the preferential folding caused by the longitudinal non-textured strip causes the formation of the aforementioned notch, which grows into a general concave region 34 as still more inflation fluid is withdrawn from the balloon. Concave region 34 is illustrated in FIGS. 17 and 18.

As more inflation fluid is withdrawn, edges 32 curl towards each other, continuing the folding pattern initiated by non-textured strip 14. The balloon C-shaped radial ridges are believed to assist in this wing curling. At the final extent of fluid withdrawal, illustrated in FIG. 19, edges 32 are curled inward and towards each other, resulting in a small profile. A balloon having two wings folded together has only about one half the profile of a balloon having flattened wings lying both in one plane. A balloon further having curled folded wings has an even smaller profile. To the extent the wing edges 32 face inward rather than outward, the possibility of damage to conduit walls is lessened.

Figure 20:
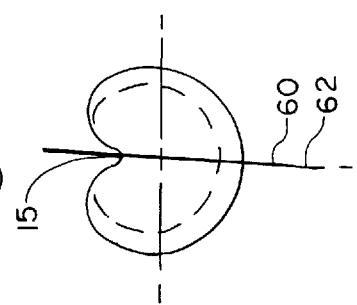
FIG. 20 is a cross-sectional diagrammatic view of a balloon taken along the plane perpendicular to the balloon longitudinal axis.
Figure 21:
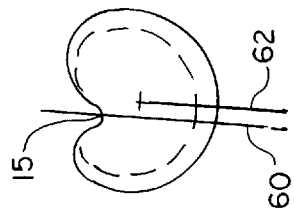
FIG. 21 is an alternative embodiment cross-sectional diagrammatic view of a balloon taken along the plane perpendicular to the balloon longitudinal axis.

In a preferred embodiment of the present invention, the surface texture comprises radially raised ridges 12. Using radially raised ridges aids in curling the balloon, as this radial surface structure is already curved, and remains curved after deflation in both the concave region 34 and on the periphery of the deflated balloon. The concave orientation of curvature in concave region 34 after deflation is opposite the convex orientation of curvature while inflated, changing abruptly at edges 32. The curved wings are illustrated in FIGS. 19, 20, and 21.

Varying geometries result in varying folding characteristics. FIG. 20 illustrates a preferred embodiment having a single longitudinal strip whereupon initial deflation the apex of the notch 15 coincides to the midline 62 when viewing the balloon cross section. FIG. 21 illustrates another preferred embodiment where notch 15 midline 60 is eccentric to balloon cross section midline 62. FIG. 21 shows a balloon cross section taken along a plane perpendicular to the longitudinal axis of the balloon. Any radial line drawn outward from the central longitudinal axis of the balloon intersects the balloon surface in a point. Well away from the notch, a surface tangent line at this point forms a right angle with the radial line. At a point closer to the notch, the tangent line angles inward toward the notch. At the points where the two tangents on either side of the notch begin to substantially angle inward, the two radii lie at a notch angle with respect to one another. In a preferred embodiment of the invention, this angle is between 1 and 180 degrees. The depth of a notch, if preformed in a balloon, in a preferred embodiment, ranges from 1 to 90% of the balloon diameter.

The present invention may also be used for stent or graft placement. Raised radial ridges may assist in maintaining a stent or series of stents in position relative to the balloon during inflation. At very high pressures, above 15 atmospheres, the ridges flatten out. This flattening ensures that the stent or graft is uniformly expanded. A textured surface also lessens adherence between graft materials such as PTFE, collagen or composites and balloon surfaces. A textured surface especially lessens adherence between expanded PTFE grafts and glassy PET balloons.

In a preferred embodiment, the balloon is formed of a thermoplastic such as polyethylene terepthalate (PET), nylon or polyethylene. Another suitable material is an elastomer. The balloon may be made using well known methods such as blow molding or co-extrusion. A multi-layer balloon may be formed using co-extrusion.

The balloon may be made by placing a pre-blown partially inflated balloon in a mold having a length corresponding to the desired length of the balloon and having a surface texture corresponding to the surface texture desired on the balloon surface. The mold is heated to the softening point of the plastic balloon material, generally between 160 degrees C and 195 degrees C. A pressurizing fluid such as nitrogen is injected into the balloon, forcing the balloon walls against the mold walls. The texture patterns form regions of greater stretching and stress on the balloon, resulting in regions of greater and lesser rigidity. The balloon is them removed from the mold. Pulling a vacuum on the balloon results in a wrapped balloon of decreased profile.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A method for expanding a stent within the vasculature of a patient comprising the steps of:

providing a balloon catheter including a catheter shaft having a distal region, a balloon disposed proximate said shaft distal region, said balloon having a length and a circumference, a balloon envelope defining a portion of said balloon, said balloon envelope having a textured surface having a texture height which varies relative to said surface over at first a portion of said length of said balloon, and at least one longitudinal reduced texture strip extending over at least said portion of said length of said balloon on said balloon surface;

providing a stent having a lumen therethrough; delivering said stent to a vessel target site within said vasculature;

advancing said balloon into said vasculature;

advancing said balloon into said stent lumen;

inflating said balloon with an inflation fluid, until said balloon is pressing against said stent;

further inflating said balloon until said stent is expanded;

removing said inflation fluid from said balloon;

preferentially folding said balloon along said reduced texture longitudinal strip;

curling said balloon envelope about said reduced texture longitudinal strip, such that said balloon has a reduced profile; and retracting said reduced profile balloon from said vasculature.

2. A method for performing angioplasty at a vessel site having vessel walls within the vasculature of a patient comprising the steps of:

providing a balloon catheter including a catheter shaft having a distal region, a balloon disposed proximate said shaft distal region, said balloon having a length and a circumference, a balloon envelope defining a portion of said balloon, said balloon envelope having a textured surface extending radially around a portion of the circumference of said balloon, said textured surface having a height which varies relative to said radial surface over at least a portion of said length of said balloon, and at least one longitudinal reduced texture strip extending over at least said portion of said length of said balloon on said balloon surface;

advancing said balloon into said vasculature near said vessel site;

inflating said balloon with inflation fluid against said vessel walls;

removing said inflation fluid from said balloon;

preferentially folding said balloon along said reduced texture strip;

curling said balloon envelope about said reduced texture longitudinal strip, such that said balloon has a reduced profile; and retracting said reduced profile balloon from said vasculature.

3. A method for retracting an inflated balloon catheter from the vasculature of a patient comprising the steps of:

providing a balloon catheter, said balloon catheter including a catheter shaft having a distal region, a balloon disposed proximate said shaft distal region wherein said balloon has a length and a circumference, a balloon envelope defining a portion of said balloon wherein said balloon envelope has a textured surface extending radially around a portion of the circumference of said balloon and wherein said textured surface has a height which varies relative to said radial surface over at least a portion of said length of said balloon, and at least one longitudinal reduced texture strip extending over at least said portion of said length of said balloon on said balloon surface, wherein said balloon is disposed within said vasculature and inflated with an inflation fluid;

removing said inflation fluid from said balloon;

preferentially folding said balloon along said reduced texture strip;

curling said balloon envelope about said reduced texture strip, such that said balloon has a reduced profile; and retracting said reduced profile balloon from said vasculature.

4. A method as recited in claim 3, wherein said balloon has a distal end, a proximal end, a first unconstrained length when not inflated and a second unconstrained length when fully inflated, wherein said second length is greater than said first length, wherein said catheter shaft includes an inner shaft and an outer shaft, each having a distal end, said inner shaft being fixedly attached to said balloon distal end, said outer shaft being fixedly attached to said balloon proximal end, said inner and outer shafts being axially moveable relative to one another, further comprising moving said inner shaft and said outer shaft distal ends apart, such that the distance between said shaft distal ends increases, such that said inflated balloon is allowed to lengthen relative to said first, not inflated length.

5. A method for making a textured balloon having a length, a circumference, and a textured surface extending radially around a portion of the circumference of the balloon, and having at least one longitudinal reduced texture strip extending over at least portion of the length of the balloon for placement on a catheter comprising the steps of:

providing a pre-blown balloon formed of a thermoplastic material, said balloon having walls, said material having a softening point temperature;

providing a mold having walls having a surface texture corresponding to said surface texture on said balloon surface;

heating said mold to said softening point temperature;

disposing said balloon within said mold;

injecting a pressurizing fluid into said balloon;

forcing said balloon walls against said mold walls; and removing said balloon from said mold.

* * * * *